(12) United States Patent
Payne

(10) Patent No.: US 7,205,442 B2
(45) Date of Patent: Apr. 17, 2007

(54) METHOD OF MAKING HIGH PURITY PHENOL

(75) Inventor: Larry Wayne Payne, Houston, TX (US)

(73) Assignee: Shell Oil Company, Houston, TX (US)

( * ) Notice: Subject to any disclaimer, the term of this patent is extended or adjusted under 35 U.S.C. 154(b) by 237 days.

(21) Appl. No.: 10/761,591

(22) Filed: Jan. 21, 2004

(65) Prior Publication Data

US 2004/0158105 A1    Aug. 12, 2004

Related U.S. Application Data

(60) Provisional application No. 60/445,528, filed on Feb. 6, 2003.

(51) Int. Cl.
    C07C 37/68    (2006.01)
(52) U.S. Cl. .................................................. 568/749
(58) Field of Classification Search ................. 568/749
    See application file for complete search history.

(56) References Cited

U.S. PATENT DOCUMENTS

| | | | | |
|---|---|---|---|---|
| 2,948,758 A | 8/1960 | Filar | ........................... | 260/621 |
| 3,029,294 A | 4/1962 | Keeble | ...................... | 260/621 |
| 3,454,653 A | 7/1969 | Larson | ...................... | 260/621 |
| 4,097,367 A | 6/1978 | Haag et al. | ................. | 208/135 |
| 5,264,636 A | 11/1993 | Shirahata et al. | ........... | 568/754 |
| 5,414,154 A | 5/1995 | Jenczewski et al. | ........ | 568/754 |
| 5,491,268 A | 2/1996 | Cipullo | ...................... | 568/758 |
| 5,502,259 A * | 3/1996 | Zakoshansky et al. | ...... | 568/754 |
| 6,489,519 B1 | 12/2002 | van Barneveld et al. | ... | 568/754 |
| 2003/0163007 A1 | 8/2003 | Dyckman et al. | ........... | 568/754 |

FOREIGN PATENT DOCUMENTS

| | | | |
|---|---|---|---|
| EP | 0568817 A2 | | 11/1993 |
| EP | 0578194 A2 | | 1/1994 |
| EP | 1088809 A1 | | 4/2001 |
| FR | 1445829 | * | 8/1965 |
| FR | 1445829 | | 6/1966 |
| GB | 676770 | * | 12/1948 |
| GB | 676770 | | 8/1952 |
| GB | 777961 | | 7/1957 |
| GB | 920864 | | 3/1963 |
| GB | 1121595 | | 7/1968 |
| JP | 58065234 | | 4/1983 |
| JP | 62-114922 | | 5/1987 |

(Continued)

OTHER PUBLICATIONS

Kirk Othmer Encyclopedia of Chemical Technology, Fourth Edition, vol. 14, pp. 737-783.

(Continued)

*Primary Examiner*—Thurman K. Page
*Assistant Examiner*—Kellette Gale

(57) ABSTRACT

A method of manufacturing a phenol product having a reduced concentration of a contaminating reaction by-product. The method includes contacting a phenol stream, having a concentration of the contaminating by-product, by contacting the phenol stream with an acidic catalyst under suitable purification reaction conditions. Also included is a composition comprising a sec-butyl benzene derived phenol product that has been purified by the removal of certain undesirable reaction by-products.

3 Claims, 1 Drawing Sheet

FOREIGN PATENT DOCUMENTS

JP            2001097901 A     4/2001

OTHER PUBLICATIONS

Figure 1:
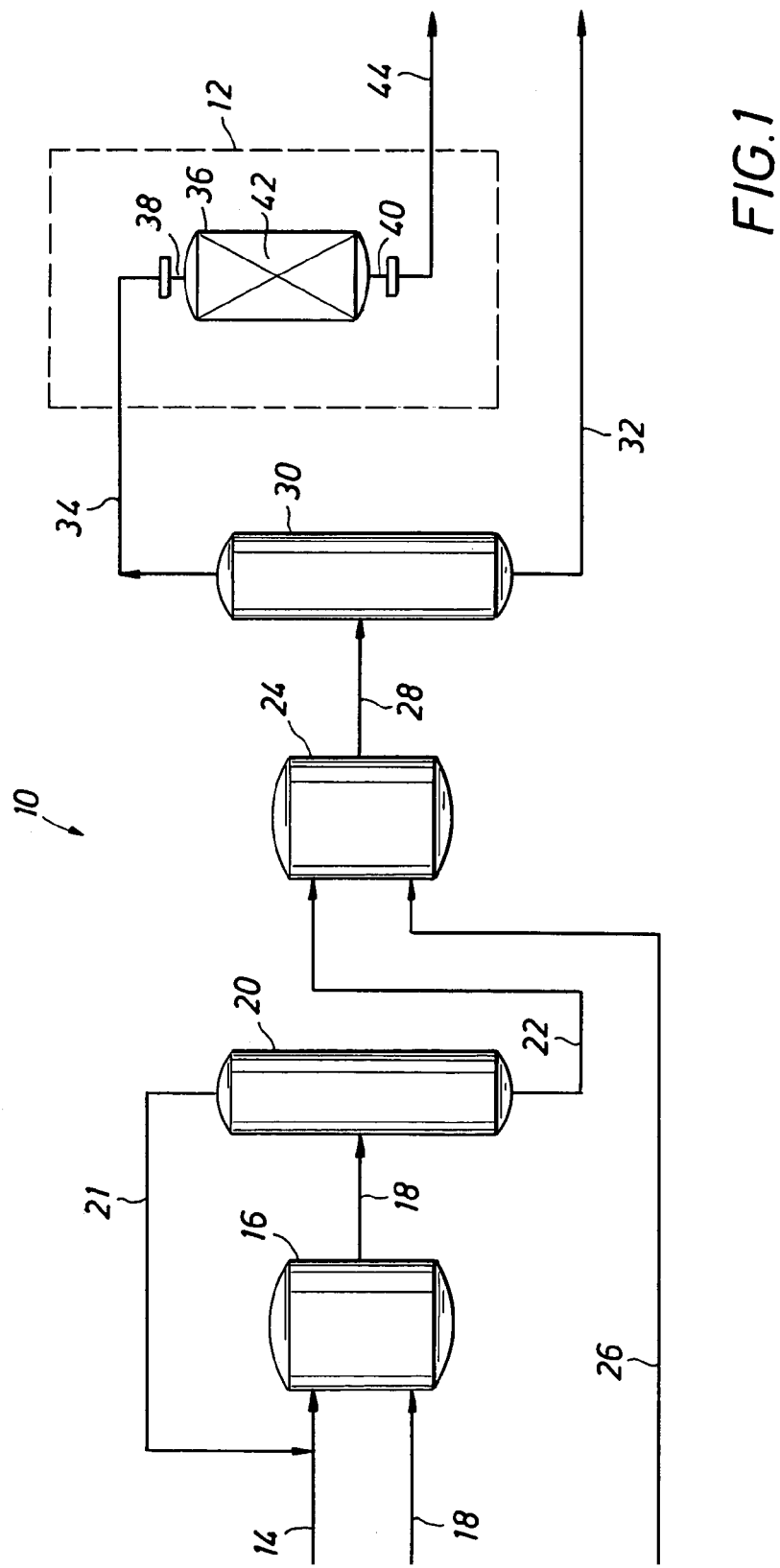

V. M. Zakoshansky et al., "Purificatioan of Phenol Derived by Cumene Peroxidation," Zeolites, Elsevier Science Publishing, US, vol. 18, No. 4, Apr. 1, 1997), p. 302.

Kirk-Othmer, Ency. Of Chem. Tech., 4$^{th}$ Ed., vol. 18, pp. 592-602.

International Search Report of Jul. 29, 2004.

Database WPI Section Ch, Week 198344 Derwent Publications Ltd., London, GB; Class A41, AN 1983-803578 XP002287062 & JP 58 065234 A (Mitsui Petrochem IND CO LTD) Apr. 18, 1983.

Kirk-Othmer Encyclopedia of Chemical Technology, Fourth Edition, vol. 16, pp. 888-923.

* cited by examiner

US 7,205,442 B2

METHOD OF MAKING HIGH PURITY PHENOL

This application claims the benefit of U.S. Provisional Application No. 60/445,528 filed Feb. 6, 2003, the entire disclosure of which is hereby incorporated by reference.

This invention relates to a method of making high purity phenol.

One known approach to manufacturing phenol includes a two-step process including the oxidation of cumene to yield cumene hydroperoxide followed by the decomposition of the cumene hydroperoxide to yield phenol and acetone. It is recognized that impurities are formed in the production of phenol using the two-step process which are difficult to remove by distillation and other methods. These impurities are undesirable; because, they cause the formation of color products when the phenol is used in downstream processes involving chlorination or sulphonation of the phenol.

It has been found that there can be benefits to using a mixed feed of cumene and sec-butyl benzene, as opposed to a cumene only feed, in the two-step process. Not only are the products of phenol and acetone produced, but the desirable and valuable product of methyl ethyl ketone is produced. The use of the mixed feed can also beneficially impact the reaction kinetics and the mix of end-product compounds of the two-step process.

While there are certainly benefits to manufacturing phenol, acetone and methyl ethyl ketone by the two-step process using a mixed feed, certain sec-butyl benzene derived and other impurities are formed that find their way into the phenol product. Examples of some of these undesirable impurities include aliphatic hydroxy carbonyl compounds, such as, hydroxy propanone, hydroxy butanone and methylcyclopentanone, and benzofurans, such as, the substituted benzofuran compounds of methylbenzofuran, ethylbenzofuran, and dimethylbenzofuran.

It is desirable to provide a process for making a high purity phenol product from a mixed feed of cumene and sec-butyl benzene.

Other aspects, objects and the several advantages of the invention will become more apparent in light of the following disclosure.

In accordance with the invention, a process is provided for purifying a phenol product. The phenol product comprises phenol and a concentration of a contaminant such as an hydroxy carbonyl compound. The phenol product is contacted under suitable reaction conditions with an acidic catalyst to thereby convert a portion of the contaminant to a reaction product.

In accordance with another invention is a composition that comprises phenol derived from sec-butyl benzene having a low concentration of contaminant by-products.

FIG. 1 is a schematic diagram illustrating a process for manufacturing phenol, acetone, and methyl ethyl ketone starting with a mixed feed of cumene and sec-butyl benzene and using the two reaction steps of oxidation followed by decomposition of certain reaction products of the oxidation step. Included in the process is a phenol purification step.

In the two-step process of making phenol, acetone and methyl ethyl ketone starting with a mixed feed of cumene and sec-butyl benzene and first oxidizing the mixed feed to yield the oxidation products of cumene hydroperoxide and sec-butyl benzene hydroperoxide followed by the decomposition of the oxidation products, undesirable reaction by-products are produced which find their way into the phenol end-product stream. Among these contaminant by-products are certain formed carbonyl compounds, such as, aliphatic hydroxy carbonyl compounds. Among these aliphatic hydroxy carbonyl compounds are hydroxy propanone and hydroxy butanone. It is an important aspect of the invention for a sufficient portion of the contaminating aliphatic hydroxy carbonyl compounds to be removed from the phenol product yielded from the two-step process in order to provide an acceptable high purity phenol product.

In one embodiment of the invention, a phenol product stream that has a concentration of a contaminating aliphatic hydroxy carbonyl compound is contacted with an acidic catalyst. This contacting step is conducted under process conditions that suitably convert a portion of the aliphatic hydroxy carbonyl compounds contained in the phenol product stream to reaction products that preferably are easier to remove from the phenol product stream. It is preferred for this conversion reaction to selectively react the aliphatic hydroxy carbonyl compounds to reaction products and to provide for the yielding of a purified phenol product having a concentration of the aliphatic hydroxy carbonyl compounds that is reduced below the concentration thereof in the phenol product stream.

Acidic catalysts useful in the inventive process are those which suitably provide for the reaction of aliphatic hydroxy carbonyl compounds contained in a phenol product stream to a reaction products that may easily be removed from the phenol product stream by separation means, such as, conventional distillation or other methods. It has been found that certain materials such as zeolites, ion exchange resins and aluminas, the aluminas of which preferably have incorporated therein a Group VIA (Cr, Co, W) metal, can be used as acidic catalysts that suitably provide for the selective reaction of aliphatic hydroxy carbonyl compounds of the phenol product stream.

Any zeolitic material can be used as an acidic catalyst of the inventive process; provided, such zeolitic material effectively provides for the treatment of the phenol by the removal or conversion of at least a portion of the concentration of the aliphatic hydroxy carbonyl compounds contained therein. Typical zeolites and their properties are described in the Kirk-Othmer Encyclopedia of Chemical Technology, Fourth Edition, Volume 16, pages 888–923, which disclosure is incorporated herein by reference. Examples of zeolites may include those having the International Zeolite Association designations FAU (zeolites X, Y), MFI (silicalite, ZSM-5), MOR (mordenite), MAZ (omega), BEA (beta), FER (ferrierite), LTA (zeolite A), GIS (zeolite B) and others.

It can be desirable for the zeolite to have a constraint index (as defined in U.S. Pat. No. 4,097,367, which is incorporated herein by reference) in the range of from about 0.4 to about 12, preferably from about 2–9. Generally, the molar ratio of $SiO_2$ to $Al_2O_3$ in the crystalline framework of the zeolite is at least about 5:1 up to infinity; but, preferably, the molar ratio of $SiO_2$ to $Al_2O_3$ in the zeolite framework is in the range of from about 8:1 to about 200:1 and, more preferably, from 12:1 to 100:1.

Preferred zeolites are those having medium or large pores generally exceeding about 4 Å (angstroms) in diameter. The most preferred zeolite are those having large pore diameters for instance exceeding 6 Å in diameter and include, for example, zeolite Y and mordenite. Suitable zeolites are commercially available from such companies as Zeolyst International who market a wide variety and range of zeolite products.

Ion exchange resins can be used as an acidic catalyst of the inventive process provided such ion exchange resins effectively provide for the treatment of the phenol product stream by the removal or conversion of at least a portion of the concentration of the aliphatic hydroxy carbonyl compounds contained therein. Typical ion exchange resins and their properties are described in the Kirk Othmer Encyclopedia of Chemical Technology, Fourth Edition, Volume 14, pages 737–783, which disclosure is incorporated herein by reference.

It is particularly desirable for the ion exchange resin to be a copolymer of styrene and divinyl benzene that is functionalized to provide an acidic ion exchange resin, or a cation exchange resin. The cation exchange resin can be either a strong acid cation exchange resin or a weak acid cation exchange resin, but the preferred ion exchange resin for use in the inventive phenol treatment method is a strong acid cation exchange resin. An example of a strong acid cation exchange resin is a sulfonated copolymer of styrene and divinyl benzene that has been functionalized with sulfonic acid groups.

Generally, a major constituent of the styrene/divinylbenzene copolymer is styrene and a minor constituent is divinyl benzene with the styrene comprising from about 75 to about 98 weight percent or more of the copolymer and the divinyl benzene comprising less than about 2 to about 25 weight percent of the styrene/divinylbenzene copolymer. Examples of suitable commercially available acidic cation exchange resins are those marketed by Mitsubishi Chemical Corporation, or its affiliates, identified as Diaion® Ion Exchange Resins such as their Diaion® SK grade resins and PK grade resins and, less preferred, Diaion® WK grade resins and WA grade resins.

Any suitable alumina or alumina-containing material can be used as an acidic catalyst of the inventive process; provided, it effectively treats the phenol product stream by the removal or conversion of at least a portion of the concentration of the aliphatic hydroxy carbonyl compounds contained therein.

It is generally desirable for the alumina to be of the type selected from, for example, alpha-alumina, beta-alumina, gamma-alumina, delta-alumina, eta-alumina, theta alumina and hydrated aluminas (such as boehmite, pseudoboehmite and bayenite). It is preferred for the alumina to be an activated alumina and selected from gamma-alumina, delta-alumina, theta-alumina, and alpha-alumina. The most preferred alumina is γ-alumina. The alumina material generally has a surface area (determined by the BET method of Brunauer, Emmett, and Teller employing $N_2$) of about 100–600 $m^2/g$, a pore volume (measured by nitrogen intrusion porosimetry) of about 0.2–1.0 $cm^3/g$, and a particle size of about 8–200 mesh or, if an extruded pellet, of any suitable size in the range, for example, of from 1 mm (1/16 inch) to 25 mm (1 inch) or more in diameter.

To help provide for the ability of the alumina to remove or convert the aliphatic hydroxy carbonyl compounds of the phenol product stream, a promoter or catalytic compound, such as a Group VIA metal, i.e. chromium, molybdenum, tungsten, can be incorporated into the alumina material to give an acidic catalyst that includes a Group VIA metal that is supported on the alumina. A metal selected from the Group VIA metals can be incorporated into the alumina by any suitable means known in the art. The resulting catalytic composition includes a Group VIA metal supported on alumina and can contain an amount of metal in the range of from 0.1 weight percent to 25 weight percent. The preferred metal component is molybdenum.

The inventive process includes treating the phenol product stream which contains a concentration of a contaminant by contacting it with the acidic catalyst, as described herein, preferably, under process or purification conditions that suitably provide for the removal of at least a portion of the contaminant. The purification conditions will vary depending upon the particular contaminant contained in the phenol product stream and upon the particular acidic catalyst used to treat the phenol product stream. If zeolitic or alumina-containing material is used as the treatment acidic catalyst, the contacting temperature can be in the range of from about 50° C. to about 250° C., preferably, from about 90° C. to about 230° C. and, most preferably, from 100° C. to 210° C. Due to the temperature sensitivity of ion exchange resins, however, when they are used as the acidic catalyst of the inventive process, the contacting temperature will tend to be in a lower temperature range of from 50° C. to 120° C.

While it is not a necessary feature of the invention for the phenol product stream to be in the liquid form when contacted with the acidic catalyst, it can be desirable for it to be substantially in the liquid phase. Thus, the contacting pressure can be such that the phenol product stream is substantially liquid and upwardly to about 689.5 kPa (100 psig). Preferably, the contacting pressure is in the range of from about 68.9 kPa (10 psig) to about 413.7 kPa (60 psig).

The phenol product stream is contacted with the acidic catalyst by any suitable manner known in the art; but, preferably, the contacting occurs within a reaction zone. The contacting can be as a batch process step or, preferably, as a continuous process step. In the latter operation, a solid bed of acidic catalyst, or a moving bed of acidic catalyst, or a fluidized bed of acidic catalyst can be employed. The contacting step, however, preferably is carried out within a reactor vessel which defines a reaction zone and contains a fixed bed of the acidic catalyst. The reactor vessel, thus, provides means for contacting the phenol product stream with the acidic catalyst under suitable contacting or purification conditions as, for example, herein described, and for yielding a treated or purified phenol product stream having a concentration of contaminant that is lower than the concentration of such contaminant in the phenol product stream.

The flow rate at which the phenol product stream is charged to the reaction zone is such as to provide a weight hourly space velocity ("WHSV") in the range of from greater than zero to about 1000 $hour^{-1}$. The term "weight hourly space velocity," as used herein, shall mean the numerical ratio of the rate at which the phenol product stream is charged to the reaction zone in pounds per hour divided by the pounds of catalyst contained in the reaction zone to which the phenol product stream is charged. The preferred WHSV of the phenol product stream to the reaction zone can be in the range of from about 0.1 $hour^{-1}$ to about 250 $hour^{-1}$, preferably, from 0.2 $hour^{-1}$ to 100 $hours^{-1}$ and, most preferably, from 0.25 $hour^{-1}$ to 25 $hours^{-1}$.

One of the significant features of the inventive process is that it solves a problem previously unaddressed relating to the purification of a phenol product stream that contains a concentration of contaminating by-products resulting from the use of sec-butyl benzene as a feed precursor to the manufacture, in particular, of phenol, and other products such as acetone and methyl ethyl ketone. Thus, the inventive process uses certain acidic catalysts to treat or purify a phenol product stream that contains a concentration of a contaminant that can be a by-product of a process for making phenol derived from sec-butyl benzene. This purified phenol product comprises phenol at a phenol concentration exceeding about 99 weight percent of the purified phenol product and, preferably, exceeding 99.5 weight percent but, most preferably, exceeding 99.8 weight percent. Additionally, the purified phenol product contains less than a contaminating concentration of aliphatic hydroxy carbonyl compounds which can be less than 10 ppmw. Preferably, the concentration of aliphatic hydroxy carbonyl compounds in the purified phenol is less than 5 ppmw and, most preferably, less than 3 ppmw or even 1 ppmw or at an undetectable concentration.

The process for making phenol can be of the type that includes the two reaction steps of oxidation of the sec-butyl benzene to provide an oxidation reaction product followed by decomposition of certain of the components of the oxidation reaction product. While it is recognized that there can be many possible reaction by-products resulting from the manufacture of phenol derived from sec-butyl benzene as the starting feed material, contaminants of particular concern are those hydroxy carbonyl compounds resulting from the use of sec-butyl benzene as a feed material, as opposed to the use of other conventional feed materials such as cumene. One particular hydroxy carbonyl compound derived from the use of sec-butyl benzene as a feed source in phenol production is hydroxy butanone.

The phenol product stream of the inventive process that is to be treated or purified using the acidic catalyst will have a contaminating concentration of a contaminant such as a contaminant by-product of a process for manufacturing phenol derived from sec-butyl benzene or derived from a mixed feed including both sec-butyl benzene and cumene. The phenol product stream can have an amount of phenol ranging from 95 weight percent upwardly to about 100 weight percent and, preferably, exceeding 98 weight percent and, most preferably, exceeding 99 weight percent of the phenol product stream.

The contaminating concentration of the contaminant can be in the range of from a contaminating concentration upwardly to about 1 weight percent of the phenol product stream to be treated and, more typically, from 3 parts per million by weight (ppmw) to 10,000 ppmw, or from 5 ppmw to 5000 ppmw. The contaminating concentration, however, can vary depending upon the particular compounds that are present as contaminants in the phenol product stream, but in the case of hydroxy butanone, a contaminating concentration can be less than or more than about 3 ppmw or in the range of from about 3 ppmw upwardly to about 10,000 ppmw. More typically, the contaminating concentration of hydroxy butanone in the phenol product stream can be in the range of from or about 5 ppmw to or about 5000 ppmw and, most typically, from 10 ppmw to 2000 ppmw.

The purified phenol product, or treated phenol product stream, can have a concentration of contaminant that is reduced below the concentration thereof in the phenol product stream to be treated in accordance with the invention. At least a portion, and preferably a major portion, of the contaminant contained in the phenol product stream is either removed from the phenol product stream or converted by reaction to another compound as a reaction product. The reaction product is preferably one that is more easily separateable from phenol by conventional distillation methods than is the contaminant. The concentration of contaminant in the purified or treated phenol product is reduced to a non-contaminating concentration which is, generally, less than or about 10 ppmw. It is desired, however, for the concentration of contaminant of the purified or treated phenol product to be less than or about 5 ppmw, but preferably, less than 3 ppmw. Most preferably, the contaminant concentration in the purified or treated phenol product is less than 1 ppmw or even at a concentration that is not detectable.

In the two-step process for making phenol and other products it is important for the feed to comprise either sec-butyl benzene or both sec-butyl benzene and cumene, either as a mixture or some other combination, in order to exploit the benefits of the two-step process. The mixed feed to the oxidation stage of the two-step process can have a wide range of concentrations for each of the components depending upon the particular product mix desired and benefits sought. Generally, the cumene concentration of the mixed feed can be in the range of from about 2 weight percent to about 98 weight percent and the sec-butyl benzene can be in the range of from about 2 weight percent to about 98 weight percent of the mixed feed. The preferred concentration range of the cumene in the mixed feed is from 10 weight percent to 90 weight percent of the total mixed feed and the preferred concentration of sec-butyl benzene is from 10 to 90 weight percent of the mixed feed. The weight ratio of sec-butylbenzene to cumene charged to the two-step process can range from 50:1 to 0.02:1.

In the first reaction stage of the two-step process the sec-butyl benzene or mixed feed is introduced into oxidation reactors which define an oxidation reaction zone. Any suitable reactor system known in the art can be used for the first reaction stage. The oxidation reaction is typically conducted without the use of a catalyst. The feed is contacted with an oxygen-containing gas under conditions that suitably convert at least a portion of the sec-butyl benzene, or both the sec-butyl benzene and cumene, to the corresponding sec-butyl benzene hydroperoxide and cumene hydroperoxide. The oxidation reaction temperature can range from about 85° C. to 150° C., preferably, from 90° C. to 145° C. and, most preferably, from 100° C. to 140° C. The oxidation reaction pressure can range from 100 kPa (14.5 psi) to 2000 kPa (290 psi) absolute. The oxidation reaction time can range from 0.5–10 hours, preferably from 1–5 hours.

The oxidation reaction effluent from the first reaction stage can, optionally, undergo a separation step by which a portion of the unreacted sec-butyl benzene and cumene, if present, of the oxidation reaction product is separated from the oxidation reaction products of sec-butyl benzene hydroperoxide and cumene hydroperoxide, if present. This optional separation step is performed by any suitable method or means for separating that is known to those skilled in the art.

The first stage oxidation reaction products are then subjected to a second stage decomposition, or cleavage, reaction step. In this second stage decomposition reaction step the sec-butyl benzene hydroperoxide is converted to phenol and methyl ethyl ketone, and the cumene hydroperoxide is converted to phenol and acetone. This decomposition step is carried out by any suitable manner known to those skilled in the art. It is preferred for the decomposition or cleavage reaction to be carried out within a cleavage reactor that defines a cleavage reaction zone within which the oxidation reaction products are contacted under suitable decomposition or cleavage reaction conditions with an acid-catalyst such as hydrogen fluoride, boron fluoride, nitric acid, hydrochloric acid, and sulfuric acid or ion exchange solid catalysts. The preferred cleavage reaction catalyst is sulfuric acid.

In the case where the feed to the two-step process comprises only sec-butyl benzene, the cleavage reaction product comprises phenol and methyl ethyl ketone. In the case of a mixed feed, the cleavage reaction product comprises phenol, acetone and methyl ethyl ketone. The cleavage reaction product is subjected to a separation step whereby the phenol product stream and a methyl ethyl ketone product stream or an acetone product stream, or both are yielded. Any suitable means known to those skilled in the art for separating the components of the cleavage reaction products can be used, but, preferably, conventional distillation methods are used to perform the separation of the cleavage reaction product components. The yielded phenol product stream can have a concentration of contaminant by-products resulting from the reaction of the starting sec-butyl benzene feed material by oxidation followed by decomposition as described herein.

Reference is now made to FIG. 1, which is a schematic representation of the two-step process 10 for making phenol and other products from a mixed feed of cumene and sec-butyl benzene. Also shown is the phenol purification system 12. In the two-step process 10, a mixed feed, comprising cumene and sec-butyl benzene, is introduced by way of conduit 14 to oxidation reaction system 16. An oxygen-containing feed comprising oxygen, which can be, for example, air, is introduced into oxidation reaction system 16 through conduit 18.

Oxidation reaction system 16 defines an oxidation reaction zone and provides means for containing the mixed feed with the oxygen-containing feed under oxidation reaction conditions suitable for the oxidation of at least a portion of the sec-butyl benzene of the mixed feed to sec-butyl benzene hydroperoxide and at least a portion of the cumene of the mixed feed to cumene hydroperoxide to yield an oxidation reaction product. The oxidation reaction product can comprise sec-butyl benzene hydroperoxide, cumene hydroperoxide, unreacted mixed feed components and secondary by-products.

The oxidation reaction product passes from oxidation reaction system 16 through conduit 18, and it is introduced into first separation system 20. First separation system 20 defines a separation zone and provides means for separating the unreacted mixed feed components and the oxidation reaction products, including sec-butyl benzene hydroperoxide and cumene hydroperoxide. The unreacted mixed feed components may be recycled back to oxidation reaction system 16 by way of conduit 21 and the thus recycled stream is introduced therein as a feed.

The separated sec-butyl benzene hydroperoxide and cumene hydroperoxide passes from first separation system 20 through conduit 22 and is introduced into decomposition, or cleavage, reaction system 24. Decomposition (cleavage) reaction system 24 defines a decomposition zone which provides for the contacting of an inorganic acid catalyst, such as sulfuric acid, with the sec-butyl benzene hydroperoxide and cumene hydroperoxide under suitable decomposition reaction conditions to thereby provide a cleavage reaction product, comprising phenol, contaminant by-products, and, optionally, acetone or methyl ethyl ketone, or both. The inorganic acid catalyst is introduced into decomposition reaction system 24 by way of conduit 24.

The cleavage reaction product passes from decomposition reaction system 24 through conduit 28 and is introduced into second separation system 30. Second separation system 30 defines a separation zone and provides means for separating the cleavage reaction product into at least two product streams, one of which is a phenol product stream, which comprises phenol and a concentration of a contaminant by-product, and the other is one or more product streams that can be an acetone product stream, or a methyl ethyl ketone product stream, or a combination stream including acetone and methyl ethyl ketone, or any combination thereof. The other product stream passes from second separation system by way of conduit 32.

The phenol product stream, or crude phenol stream, which comprises phenol and contaminant by-product, passes from second separation system 30 through conduit 34 and is introduced or charged to phenol purification system 12. Phenol purification system 12 can include one or more separators, such as distillation columns, and one or more reactors, all arranged in any suitable configuration. As shown in FIG. 1, however, only a single phenol purification reactor 36 is illustrated. Phenol purification system 12, thus, includes a phenol purification reactor 36. Phenol purification reactor 36 is equipped with an inlet 38 and an outlet 40 and defines a phenol purification reaction zone. Contained within the phenol purification reaction zone is a suitable acid catalyst for converting at least a portion of the contaminant by-product contained in the phenol product stream to a reaction product. Conduit 34 is connected in fluid flow communication between second separation system 30 and phenol purification system 12. The phenol purification reactor 36 provides means for contacting the phenol product stream with an acid catalyst under reaction or purification conditions suitable for converting at least a portion of the contaminant contained in the phenol product stream to a reaction product to thereby provide a purified phenol product stream having a reduced concentration of contaminant. The purified phenol product is yielded as an effluent stream from phenol purification reactor 36 through conduit 44 which is connected in fluid flow communication with outlet 40 of phenol purification reactor 36.

The following examples are intended to illustrate the present invention and are not intended to unduly limit the scope of the invention.

EXAMPLES

Examples 1–6 describe the experimental procedure used to measure the effectiveness of various materials in treating a phenol product that contains a contaminant concentration of hydroxyketones. These Examples show that zeolites, cation exchange resins and alumina can be effectively used to convert the hydroxyketones contained in the phenol product.

In the following Examples 1–6 a pure, anhydrous phenol was used which was collected from a side-draw product stream of a phenol distillation column of a commercial process for manufacturing phenol from cumene. Feeds for each of the examples were prepared by adding small amounts of hydroxyketone impurities using available reagents. The phenol feed was then contacted in the liquid phase by stirring with a catalyst in the amount of 2 percent based on phenol weight for a period of time and at temperatures in the range of 50–150° C. The reaction product mixture was then cooled, filtered, and analyzed by gas chromatography for the individual hydroxyketones and the corresponding benzofuran derivatives.

Example 1

Cation Resin

A feed containing 1450 ppm hydroxyacetone (HA or acetol), 520 ppm of 1-hydroxy-2-butanone (1HB), and 540 ppm of 3-hydroxy-2-butanone (3HB or acetoin) was prepared from pure phenol. The feed was stirred for 2 hours at 80° C. with Amberlyst 15 (TM) cation exchange resin beads which had previously been water rinsed and vacuum dried. Conversion of the hydroxyketones was 94 percent for HA, 74 percent for 1HB, and 80 percent for 3HB. Approximately 6 percent of the HA was converted to 2-MBF (2-methyl benzofuran), 3 percent of the 1HB was converted to EBF (2-ethyl benzofuran), and 24 percent of the 3HB was converted to DMBF (1,3 dimethyl benzofuran).

Example 2

Zeolite

A feed containing 1000 ppm HA, 5300 ppm of 1HB, and 1050 ppm of 3HB was prepared from pure phenol and contacted for 2 hours at 150° C. with a Y-zeolite catalyst which had been previously activated and dried. The percent conversions of hydroxyketones were 93 for HA, 84 for 1HB, and 89 for 3HB. The corresponding benzofuran selectives were 33, 18 and 68 percent.

Example 3

8% Mo on γ-Alumina Containing 1–2% Dispersed Silica

A feed containing 990 ppm HA, 520 ppm of 1HB, and 490 ppm of 3HB was prepared from pure phenol and contacted for 2 hours at 145° C. with an alumina catalyst containing approximately 8 percent molybdenum. The catalyst was previously activated and dried. Conversion of hydroxyketones averaged 98, 98, and 100 percent for HA, 1HB, and 3HB, respectively, for three separate experiments. The corresponding benzofuran selectivities averaged approximately 6, 3, and 3 percent.

Example 4

4% Mo on γ-Alumina Containing 1–2% Dispersed Silica

A feed containing 990 ppm HA, 520 ppm of 1HB, and 490 ppm 3HB was prepared from pure phenol and contacted for 2 hours at 145° C. with an alumina catalyst containing approximately 4 percent molybdenum. The catalyst was previously activated and dried. Conversion of hydroxyketones were 84, 87 and 98 percent for HA, 1HB, and 3HB. The corresponding benzofuran selectivities averaged approximately 6, 3, and 2.5 percent.

Example 5

Alumina Only

A feed containing 990 ppm HA, 520 ppm of 1HB, and 490 ppm of 3HB was prepared from pure phenol and contacted for 2 hours at 145° C. with an alumina catalyst containing no molybdenum and which had been previously activated and dried. Conversion of hydroxyketones averaged 18, 15, and 8 percent for HA, 1HB, and 3HB, respectively, for three separate experiments. The corresponding benzofuran selectivities were approximately 2, 0.5, and 2 percent.

Example 6

Blank—Heat but no Catalyst

A feed containing 990 ppm HA, 520 ppm of 1HB and 490 ppm of 3HB was prepared from pure phenol and heated for 2 hours at 145° C. without addition of a catalyst. Conversion of hydroxyketones averaged 5, 5, and 7 percent for HA, 1HB, and 3HB, respectively, for three separate experiments. The corresponding benzofuran selectivities averaged approximately 3, 0.1, and 3 percent.

The following table summarizes the results from the above tests.

TABLE I

Conversion of the Hydroxyketone Contained in a Phenol Product Using Different Catalyst

| | % Conversion of hydroxyketones | | | % Selectivity to benzofuran | | |
|---|---|---|---|---|---|---|
| | HA | 1HB | 3HB | HA | 1HB | 3HB |
| 8% Mo on alumina | 98 | 98 | 100 | 6 | 3 | 3 |
| 4% Mo on alumina | 84 | 87 | 98 | 6 | 3 | 2.5 |
| alumina only | 18 | 15 | 8 | 2 | 0.5 | 2 |
| no catalyst | 5 | 5 | 7 | 3 | 0.1 | 3 |
| cation exchange resin | 94 | 74 | 80 | 6 | 3 | 24 |
| zeolite | 93 | 84 | 89 | 33 | 18 | 68 |

The conversion data presented in Table I above show the advantages from using either a zeolite, cation exchange resin or molybdenum on alumina in the treatment of a phenol product that contains a concentration of hydroxyketone when compared to the use of alumina or of no treatment catalyst. As can be observed, the conversion of hydroxyketones using the zeolite, cation exchange resin and molybdenum on alumina catalyst all exceeded 80 percent and even 90 percent. The alumina only catalyst provided a conversion of less than 20 percent. The conversion of hydroxyketones when no catalyst was used was less than 10 percent.

While this invention has been described in terms of the presently preferred embodiment, reasonable variation and modifications are possible by those skilled in the art. Such variations and modifications are within the scope of the described invention and appended claims.

That which is claimed is:

1. A method of making a high purity phenol product, said method comprises:
    subjecting a mixed feed comprising cumene and sec-butyl benzene to oxidation conditions to yield an oxidation reaction product comprising sec-butyl benzene hydroperoxide and cumene hydroperoxide;
    subjecting at least a portion of the sec-butyl benzene hydroperoxide and cumene hydroperoxide of said oxidation reaction product to decomposition reaction conditions to yield a cleavage reaction product comprising phenol, acetone, and methyl ethyl ketone;
    separating said cleavage reaction product into at least a phenol product stream and another product stream wherein said phenol product stream comprises at least a portion of said phenol of said cleavage reaction product and a contaminant by-product; and
    contacting under suitable purification reaction conditions said phenol product stream with an acid catalyst to thereby convert at least a portion of said contaminant by-product to a reaction product.

2. The method of claim 1 wherein said acid catalyst is selected from the group of catalyst materials consisting of zeolite compounds, cation exchange resins and aluminas.

3. The method of claim 1 wherein said contaminant by-product includes hydroxy butanone.

* * * * *